United States Patent
Quevedo et al.

(10) Patent No.: US 9,241,738 B2
(45) Date of Patent: *Jan. 26, 2016

(54) CAM LOCK PEDICLE SCREW

(71) Applicant: ROLIX Holdings, LLC, Pinecrest, FL (US)

(72) Inventors: Felix Quevedo, Pinecrest, FL (US); Roberto Salvat, Jr., Wellington, FL (US)

(73) Assignee: Rolix Holdings, LLC, Pinecrest, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/097,813

(22) Filed: Dec. 5, 2013

(65) Prior Publication Data

US 2014/0094857 A1 Apr. 3, 2014

Related U.S. Application Data

(63) Continuation of application No. 12/953,121, filed on Nov. 23, 2010.

(60) Provisional application No. 61/263,671, filed on Nov. 23, 2009.

(51) Int. Cl.
*A61B 17/70* (2006.01)
*A61B 19/00* (2006.01)
*A61B 17/00* (2006.01)

(52) U.S. Cl.
CPC ........... *A61B 17/7037* (2013.01); *A61B 17/701* (2013.01); *A61B 17/7032* (2013.01);
(Continued)

(58) Field of Classification Search
CPC ............. A61B 17/701; A61B 17/7032; A61B 17/737; A61B 17/7076; A61B 17/7077; A61B 17/7082; A61B 19/2203; A61B 19/26; A61B 2017/00212; A61B 2019/2292; A61B 2019/302; A61B 2019/307; A61B 2019/524
USPC ........ 606/264–278, 305–308, 319–328, 86 A
See application file for complete search history.

(56) References Cited

U.S. PATENT DOCUMENTS

| | | |
|---|---|---|
| 5,443,467 A | 8/1995 | Biedermann et al. |
| 5,474,555 A | 12/1995 | Puno et al. |

(Continued)

FOREIGN PATENT DOCUMENTS

WO WO2006047707 5/2006

*Primary Examiner* — Pedro Philogene
(74) *Attorney, Agent, or Firm* — Mchale & Slavin, P.A.

(57) ABSTRACT

The present invention is directed to a pedicle screw fixation system which can be made for either posterior cervical, thoracic, lumbar spine, or elsewhere. With this type of system a surgeon can implant a pedicle screw system utilizing the same instrument set for an open or closed procedure. The system is designed to avoid cross threading and splitting of tulip heard by use of an outer threaded tulip and reducing donut. The system also provides the ability for superior angulation for hard to reach areas that are common in spinal procedures. The system allows for a bio-absorbable part (the reduction donut) that enhances fusion in the coming months after the procedure. With the elongate tulip portion of the system the user is able to avoid the need for other cannula type instruments; the need of additional parts; the need of additional instruments which could introduce bacteria into the patient and the need for fluoroscopy. The system is completely cannulated so as to permit a HOLDING wire driven procedure. The rods employed with these pedicle screws can be either flexible or rigid. Preferably a rod which is octagonal in cross section is employed with the system so as to prevent rotation in the tulip and slippage.

24 Claims, 10 Drawing Sheets

(52) U.S. Cl.
CPC ......... *A61B17/7076* (2013.01); *A61B 17/7077* (2013.01); *A61B 17/7082* (2013.01); *A61B 19/2203* (2013.01); *A61B 19/26* (2013.01); *A61B 2017/00212* (2013.01); *A61B 2019/2292* (2013.01); *A61B 2019/302* (2013.01); *A61B 2019/307* (2013.01); *A61B 2019/524* (2013.01)

(56) References Cited

U.S. PATENT DOCUMENTS

| | | |
|---|---|---|
| 5,549,608 A | 8/1996 | Errico et al. |
| 5,554,157 A | 9/1996 | Errico et al. |
| 5,586,984 A | 12/1996 | Errico et al. |
| 5,672,176 A | 9/1997 | Biedermann et al. |
| 5,683,392 A | 11/1997 | Richelsoph et al. |
| 5,688,274 A | 11/1997 | Errico et al. |
| 5,690,630 A | 11/1997 | Errico et al. |
| 6,413,258 B1 | 7/2002 | Bernhardt, Jr. |
| 6,471,705 B1 | 10/2002 | Biedermann et al. |
| 6,551,323 B2 | 4/2003 | Doubler et al. |
| 6,623,485 B2 | 9/2003 | Doubler et al. |
| 6,695,843 B2 | 2/2004 | Biedermann et al. |
| 6,840,940 B2 | 1/2005 | Ralph et al. |
| 7,090,674 B2 | 8/2006 | Doubler et al. |
| 7,105,029 B2 | 9/2006 | Doubler et al. |
| 7,211,086 B2 | 5/2007 | Biedermann et al. |
| 7,334,961 B2 | 2/2008 | Doubler et al. |
| 7,335,201 B2 | 2/2008 | Doubler et al. |
| 7,438,715 B2 | 10/2008 | Doubler et al. |
| 8,075,590 B2 | 12/2011 | Janowski et al. |
| 8,623,061 B2 * | 1/2014 | Quevedo et al. ............... 606/272 |
| 2002/0082602 A1 | 6/2002 | Biedermann et al. |
| 2003/0125741 A1 * | 7/2003 | Biedermann et al. ........... 606/61 |
| 2004/0158247 A1 * | 8/2004 | Sitiso et al. ..................... 606/61 |
| 2006/0235393 A1 * | 10/2006 | Bono et al. ..................... 606/61 |
| 2007/0055235 A1 | 3/2007 | Janowski et al. |
| 2008/0045953 A1 | 2/2008 | Garamszegi |
| 2009/0125072 A1 | 5/2009 | Neubardt |
| 2011/0125951 A1 | 5/2011 | Youngworth |
| 2011/0126268 A1 | 5/2011 | Youngworth |
| 2011/0126269 A1 | 5/2011 | Youngworth |

\* cited by examiner

CAM LOCK PEDICLE SCREW

CROSS REFERENCE TO RELATED APPLICATIONS

In accordance with 37 C.F.R. 1.76, a claim of priority is included in an Application Data Sheet filed concurrently herewith. Accordingly, the present invention is a continuation application that claims priority to U.S. patent application Ser. No. 12/953,121, filed Nov. 23, 2010, entitled "CAM LOCK PEDICLE SCREW", which claims priority of U.S. Provisional Patent Application No. 61/263,671, filed Nov. 23, 2009, entitled "CAM LOCK PEDICLE SCREW", the entirety of which is incorporated herein by reference.

FIELD OF THE INVENTION

The invention relates generally to screws and coupling elements for use with orthopedic fixation systems. More particularly, the invention relates to a pedicle screw and a coupling element for use with an orthopedic rod implantation device. The locking element is on the head of the pedicle screw and locks the orthopedic rod to the pedicle screw such that the orthopedic rod is fixed relative to the pedicle screw and an individual's spine.

BACKGROUND OF THE INVENTION

Human spinal columns comprise an upper portion having in excess of 20 individual bones, and a lower portion comprising the sacral bone and the coccygeal bodies. Scoliosis is a medical condition in which an individual's spine becomes curved from side to side, laterally, and becomes shaped like a "C" or an "S". The spine can also rotate about its vertical axis. This is a very painful condition in adults. Scoliosis is typically classified as congenital (caused by vertebral anomalies at birth), idiopathic (sub-classified as infantile, juvenile, adolescent or adult according to when onset occurs) or as having developed as a secondary symptom of another condition, such as spina bifida, cerebral palsy, spinal muscular atrophy or due to physical trauma.

While the most common form of scoliosis is adolescent idiopathic scoliosis, there is no clear common cause. Scoliosis, when present in an individual, worsens during the adolescent growth spurt. Also, during adolescence, due to rapid growth of the body, hip and leg proportions in the leg and thigh may become misaligned, causing temporary scoliosis. If left untreated, scoliosis can be very painful in adulthood due to the muscles trying to conform to the abnormal curvature of the spine.

While doctors do not always recommend surgery as the treatment for scoliosis, it is the most efficient method of straightening the spine. Scoliosis surgery may be performed for cosmetic reasons rather than to relieve or prevent pain. Spinal fusion is currently the most widely performed surgery for the treatment of scoliosis. This technique may be performed from the anterior (front) of the spine, from the posterior (back) of the spine or a combination of anterior and posterior. The goals of this surgery include stabilization of spinal segments (i.e. vertebrae), deformity correction within safe parameters and enhancement of spinal fusion. One of the techniques employed in spinal fusion utilizes pedicle screws inserted into the vertebrae, and stabilization rods secured to and spanning a plurality of pedicle screws.

Other types of problems related to the human spine include injury or deterioration of the discs located between the vertebrae. One procedure to correct these problems is to remove the damaged or deteriorated discs and fuse adjacent vertebras together. This procedure is similar to the treatment of scoliosis, but it involves a smaller number of vertebrae. Pedicle screws and stabilization rods are employed in this procedure also.

DESCRIPTION OF THE PRIOR ART

Ralph et al., U.S. Pat. No. 6,840,940 discloses a screw and coupling element assembly for use with an orthopedic rod implantation device which includes a screw with a head and a shaft extending from the head, a coupling element with a seat within which the head is seatable such that the shaft protrudes from the coupling element, and a locking element mateable with the coupling element and when mated is selectively movable through a plurality of positions including unlocked and locked positions. When in the unlocked position, the locking element presents a rod-receiving channel and the head is movable in the seat such that the shaft is directable in a plurality of angles relative to the coupling element. When in the locked position, a rod disposed within the rod-receiving channel is fixed relative to the coupling element and the head is immovable in the seat such that the shaft is fixed at an angle relative to the coupling element. There are no external threads on coupling element 150.

Errico et al., U.S. Pat. No. 5,688,274, discloses a hook and rod device for implantation and fixation to the centerline of the spine, wherein the rod provides for immobilization of the spine via its inherent rigidity. The hook elements are designed to be mounted at the arched portion of the lamina. In a first plow shaped embodiment, the blade portion of the hook is an arched surface which seats under the arched surface of the lamina. In a second claw shaped embodiment, the blade portion includes a bifurcated conformation having a pair of offset flat extending members which are offset so as to seat under the angled portions of the lamina which are directly laterally disposed relative to the arched center of the lamina. The rod coupling features of the hooks may further be polyaxial by virtue of separate coupling elements which may be mounted to the blade portion, for example on a semi-spherical head portion thereof. In the alternative embodiment, the blade portion may have a contractible recess formed in a top thereof, for receiving and locking to a shaft of body portion at a variety of heights. The rod receiving features of the hook may include both the polyaxial and height variability natures of both of the previous hooks by having a shaft portion which has a semi-spherical head onto which the coupling element is mounted. The locking element does not rotate about a horizontal axis.

Janowski et al., U.S. Published Patent Application No. 2007/0055235 discloses a spinal fixation system which includes a coupling member having a CAM lock member that is fixed against translation therealong as it is turned with turning of the CAM lock member causing an elongate member such as a spinal rod to be pushed downward in the coupling member for fixing the rod therein. In another embodiment, the rod is fixed against a low profile insert that seats in a recess formed in the head of an anchor member projecting from the coupling member. The insert has an upper surface against which the rod is fixed, and that in one form is flat to provide for line contact against the rod so as to minimize damage thereto. In another form, the CAM lock member CAMs against a clamping member driving it downward in the coupling member for fixing the rod therein. The locking element does not rotate about a horizontal axis.

Biedermann et al., U.S. Pat. No. 5,672,176, discloses an anchoring member for connecting a rod with a bone which includes a screw member having a treaded portion and a screw head with a spherical segment-shaped portion, a seat part receiving said screw head of said screw member and said rod, and a pressure member formed to embrace said screw head from its side opposite to said threaded portion. The seat part has a first end, a second end opposite to said first end, an axis of symmetry passing through said first and second end, and a bore which is coaxial with said axis of symmetry for passing said threaded portion therethrough and has a first portion adjacent to said first end, said first portion having a substantially U-shaped cross-section with two free legs with an internal screw thread for receiving said rod therebetween. The seat part further has a second portion adjacent to said second end, said second portion tapering towards the second end with a predetermined cone angle, and a pressure member has an outer conical surface in a region laterally surrounding said screw head, said conical surface tapering towards said second end with a cone angle corresponding to said predetermined cone angle.

Biedermann et al., U.S. Pat. No. 6,471,705, discloses a bone screw having a threaded portion and a reception part for receiving a rod to be connected to the bone screw. The securing and locking action of the connection between the bone screw and the rod is provided by an exterior nut. To provide for the required strength and durability of the connection, the exterior nut comprises an inside sleeve-shaped element having a predetermined inner dimension and an outer diameter which is almost equal to or slightly less than the diameter of the bore, and a pressure element arranged therein. The pressure element comprises a first section at its end facing the bottom of the bore hole. The outer dimension of the first section is greater than the predetermined inner dimension and the first section causes the element to be expanded when pressure is exerted on the rod to be received.

Biedermann et al., U.S. Published Patent Application No. 2002/0082602, discloses a bone screw, which is very similar to the Biedermann et al. U.S. Pat. No. 6,471,705.

Bono et al., U.S. Published Patent Application no. 2006/0235393 discloses an assembly such as an anchor screw, bone plate, offset hook, post, transverse connector for anchoring to bone and clamping a linkage such as a rod or wire cable to the anchoring member. The assembly has a top member with an open slot to receive the linkage, and a twist-lock closure cap to close the open end, capturing the linkage in the slot. One closure cap fits over and around the top member, with a set of segmented protrusions that extend through a corresponding set of protruding flange segments spaced about the circumference of the top member. The cap is configured to rotate and lock against the top member like a flange-locking bayonet mount when turned through a limited degree of rotation. Slots may be provided through the face of the closure cap allowing reduction tabs to project through the cap, and the locking cap may be adapted to a range of screw, eye, hook, post, connector and other anchor assemblies to securely clamp the linkage by use of a rotation tool disposed along an access path aligned with the axis of the screw, thus requiring no lateral clearance along the longitudinal direction of the linkage element. Locking is effected by a set screw that passes through the cap and tightens against the linkage to firmly immobilize it in the anchor assembly. Another cap embodiment fits into the center of the head with a partial twist locking motion. Opposed locking surfaces prevent slippage in the radial direction, and a sloping contact floor surface may apply torque to further increase pressure on mating detent features in an adjacent wall.

Garamszegi, U.S. Published Patent Application No. 2008/0045953 discloses a bone stabilizer assembly which includes a fixation element, a coupling element, and a compression nut. The fixation element engages a bone and has a head portion and shank portion. The coupling element has an internal bore sized to receive the shank portion of the fixation element and a pyramid-shaped seat for supporting the head portion of the fixation element. The coupling element is constructed to receive a stabilizer rod. The compression nut engages the coupling element and can rotatingly move distally into the coupling element to translate a force to the head portion through the rod and the saddle such that the head portion is forced against the seat of the coupling element to prevent relative movement between the fixation element and the coupling element.

Puno et al., U.S. Pat. No. 5,474,555; Errico et al., U.S. Pat. No. 5,549,608; Errico et al., U.S. Pat. No. 5,554,157; Errico et al., U.S. Pat. No. 5,586,984, and Errico et al., U.S. Pat. No. 5,690,630 are also prior art pedicle screw systems.

SUMMARY OF THE INVENTION

The present invention is directed to a pedicle screw fixation system which can be made for either posterior cervical, lumbar spine, or elsewhere. With this type of system a surgeon can implant a pedicle screw system utilizing the same instrument set for an open or closed procedure. The system is designed to avoid cross threading and splitting of tulip head by use of an outer threaded tulip and reducing donut. The system also provides the ability for superior angulation for hard to reach areas that are common in scoliosis or open procedures. The system allows for a bio-absorbable part (the reduction donut) that enhances fusion of the vertebrae in the coming months after the procedure. With the elongate tulip portion of the system, the user is able to avoid the need for other cannula type instruments; the need of additional parts; and the need of additional instruments for insertion, reduction, and other tooling which could introduce bacteria into the patient and minimize the need for fluoroscopy. The system is completely cannulated so as to permit a K-wire driven procedure. The rods employed with these pedicle screws can be either flexible or rigid. Preferably a rod which is octagonal in cross section is employed with the system so as to prevent rotation in the tulip and slippage.

Accordingly, it is an objective of the present invention to provide a pedicle screw system which is minimally invasive and permits last minute adjustment prior to insertion of the system.

It is a further objective of the present invention to provide a pedicle screw system wherein the tulip does not have any inner threads.

It is a further objective of the present invention to provide a pedicle screw system wherein there is the ability to incorporate a uniplanar, monoaxial, polyaxial, and any other type of pedicle screw system configuration.

It is yet another objective of the instant invention to provide a pedicle screw system wherein cross threading of the inner tulip is prevented.

It is a still further objective of the present invention to provide a pedicle screw system wherein flailing out of the tulip head is prevented, thus avoiding breakage of the tulip head and subsequent removal of the broken system and replacement with another system.

It is a still further objective of the present invention to provide a pedicle screw system wherein there is no stripping of a screw or set screw.

It is a still further objective of the present invention to provide a pedicle screw system wherein there is no need for extra tooling with regards to doing an open case versus percutaneous implementation of screws.

It is a still further objective of the present invention to provide a pedicle screw system which utilizes a standard CAM locking mechanism for set screw and rod fixation.

It is a still further objective of the invention to provide a pedicle screw system wherein the tulip can be elongate so that it can be manipulated outside of the wound.

It is a still further objective of the present invention to provide a pedicle screw system wherein when the surgeon is finished manipulating the tulip, a reduction nut is employed to secure the rod in place and an inner locking CAM is closed to permit an elongate portion of the tulip to be snapped off.

It is a still further objective of the present invention that, as a reduction nut or reduction sleeve is employed to secure the rod in place, the process enables the device to reduce the deformity by bringing an upward force on the pedicle screw which in turn manipulates the vertebral body. This will allow for more control of the reduction making it safer and easier to reduce the deformity by simply turning the reduction nut or threaded sleeve.

It is a still further objective of the present invention to provide a system whereby the pedicle screws and rods can be robotically installed while the surgeon is at a remote location.

Other objects and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

DETAILED DESCRIPTION OF THE INVENTION

While the present invention is susceptible of embodiment in various forms, there is shown in the drawings and will hereinafter be described a presently preferred, albeit not limiting, embodiment with the understanding that the present disclosure is to be considered an exemplification of the present invention and is not intended to limit the invention to the specific embodiments illustrated.

Figure 1:
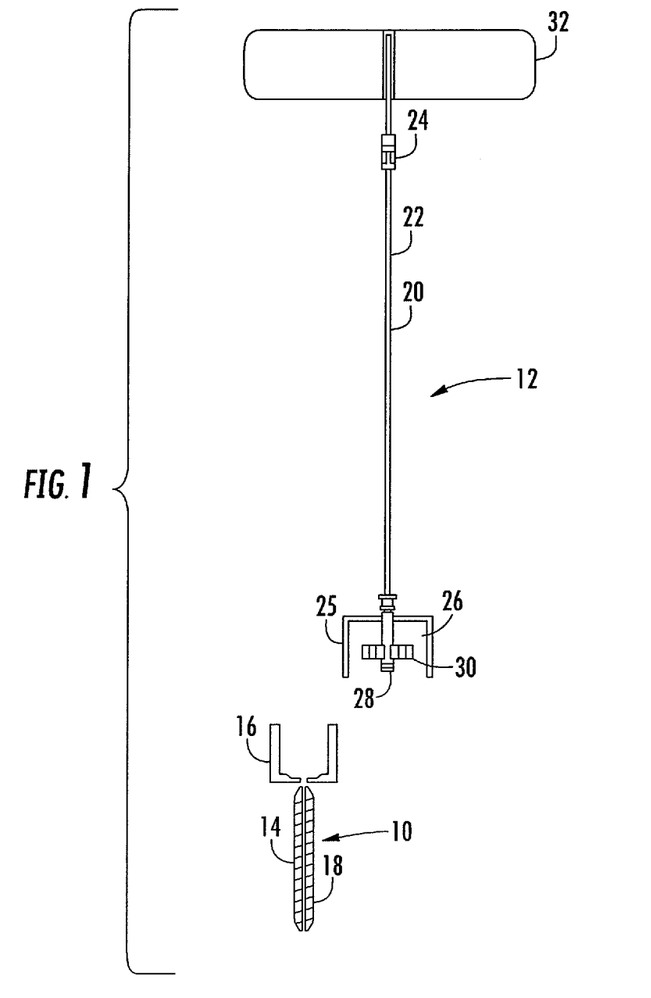
FIG. 1 is the pedicle screw system of the present invention including a tool used to install the pedicle screw.

Referring now to FIGS. 1-33, a pedicle screw fixation system will now be described. FIG. 1 illustrates a typical pedicle/bone screw fixation system 10 and a tool 12 used to install the pedicle/bone screw fixation system in an individual. The system of the present invention can be used in both minimally invasive and open procedures, remote surgery, or in the use of robotics. The pedicle screw fixation system can be used for posterior cervical, thoracic, lumbar spine or elsewhere. One of the advantages of the present invention is that the same fixation system and installation tool can be utilized in both open and closed procedures.

One of the features of the present invention is the use of a tulip including threads on the outer surface of the tulip 16 and a reduction donut 44 or reduction threaded sleeve 60. This feature is designed to avoid cross-threading and splitting of the tulip. This feature is also designed to allow for an easy and controlled method of vertebral reduction with the manipulation of the reduction donut or threaded reduction sleeve. This type of system affords the surgeon the ability for superior angulation for hard to reach areas which are common in scoliosis procedures. Another feature of the present invention is a reduction donut that is secured to the outer portion of the tulip. In addition to assisting in securing a rod in the tulip, it avoids splitting of the tulip by compressing the tulip. Many prior art systems employ a set screw inside of the tulip to secure the stabilization rod to the pedicle screw. When the set screw is tightened to the torque necessary to retain the rod, it sometimes splits the tulip because of the angles of the threads on the set screw and the angles of the threads on the interior of the tulip. These two angles produce a radially outward force relative to a centerline of the tulip, thus moving the tulip radially outward relative to the set screw. This function is now replaced by an interlocking CAM 40 located on the inside of the tulip. The reduction donut of the present invention also helps to avoid this problem by surrounding the exterior of the tulip and applying pressure radially inwardly and downwardly toward the rod as it is tightened. In a growing rod system, the reduction nut can or cannot be used and the interlocking CAM can be left open or partially closed. The reduction donut can also be made from a bio-absorbable material 52 which would enhance fusion between the stabilization rod 50 and the pedicle screw system. The system of the present invention is preferably completely cannulated to permit a HOLDING wire driven procedure. This system can be utilized with either rigid and flexible rods, or interconnectors between vertebral bodies. The rods employed with the present invention can be octagonal in cross-section, but may be any other shape in cross-section.

FIG. 1 illustrates the pedicle screw fixation system 10 of the present invention and a tool or instrument 12 used to insert the pedicle screw system into an individual and secure a stabilization rod to the pedicle screw 14. Whenever a minimally invasive procedure is to be employed, the surgeon preferably utilizes a Jamshidi needle (not shown) to insert HOLDING wire (not shown) into the pedicle of an individual into which a pedicle screw will be placed. A fluoroscope normally will be employed to locate the pedicle or pedicles or through robotic tactile manipulation into which the pedicle screws will be inserted. A depth gauge associated with the Jamshidi needle helps the surgeon or robot determine the depth that the HOLDING wire will be inserted into the pedicle or pedicles. After the HOLDING wire is secured to the pedicle, the surgeon removes the Jamshidi needle. The pedicle screw and tulip of the present invention are placed onto the HOLDING wire and guided into position.

The pedicle screw 14 illustrated in FIG. 1 is provided with a hollow core 18 along its length. The HOLDING wire is passed through this hollow core to help position the pedicle screw on the pedicle of a vertebra of an individual. Prior to insertion of the pedicle screw, a tap (not shown) which also has a hollow core, is inserted onto the HOLDING wire and starts a hole in the pedicle of a vertebra into which the pedicle screw is to be inserted. After the initial hole is made, the tap is removed. The tool or instrument 12 used to install the pedicle screw of the present invention is also provided with a hollow core 20 along its shaft. The HOLDING wire is passed through this hollow core 20 to help position the tool 12 within the individual so as to align the tool and the pedicle screw to enable correct placement of the pedicle screw. The driver shaft 22 of the tool 12 is cannulated to allow for MIS adaptability. A locking mechanism 24 is located toward an upper portion of the drive shaft. The locking mechanism is employed to lock the outer retainer sleeve and prevent it from rotation. The retainer sleeve 25 is located at the lower portion of the tool 12. The retainer sleeve 25 includes threads 26 on an inner surface. These threads are designed to mate with threads 17 on an outer surface of a tulip 16 (FIG. 11), which will be described hereinafter. Tool 12 further includes a mechanism 28 which is designed to engage the head 15 (FIG. 10) of the pedicle screw 14 and drive the pedicle screw 14 into the bone. The mechanism 28 can also be employed to remove the screw 14 from the bone should the need arise. Another mechanism 30 is located at a lower portion of the tool 12. The mechanism 30 is located on the shaft 22 and inwardly of retainer sleeve 25. Mechanism 30 is designed to engage the inner portion of the tulip 16 associate with the pedicle screw. There are no threads on the inner surface of the tulip 16 of the present invention as compared to the prior art tulips which have threads on their inner surface. Handle 32 located at the top of tool 12 is employed to drive the screw into a bone, remove the screw from a bone and secure the locking mechanism 24 onto tulip 16 of the pedicle screw assembly. After the pedicle screw and tulip of the present invention are installed on the pedicle or other bone, the HOLDING wire is removed and the remainder of the procedure is completed. Next, a stabilization rod is placed within the U-shaped interior of the tulip. A reduction nut is now secured to the tulip in a counter-clockwise torque motion. Preferably, it is threaded to the outer surface of the tulip tube extension. The reduction nut is threaded or moved downwardly toward the lower portion of the tulip. In certain situations a reduction sleeve is utilized to rotate and thread the reduction nut toward the lower portion of the tulip. When the stabilization rod is in the final position, as determined by the surgeon, a retention member secures the stabilization rod to the tulip. The CAM lock is rotated in a clockwise torque motion and the reduction nut is now tightened counter-clockwise to its final predetermined torque. Next, excess portions of the tulip above the reduction nut are removed from the tulip.

Figure 2:
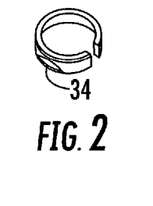
FIG. 2 is a reduction nut of the present invention.
Figure 3:
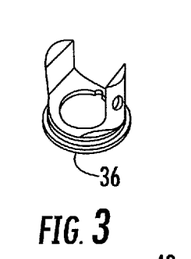
FIG. 3 is a saddle assembly of the present invention.
Figure 4:
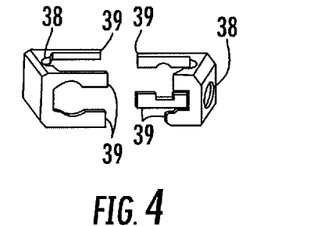
FIG. 4 is a retention member of the present invention in its open position.
Figure 10:
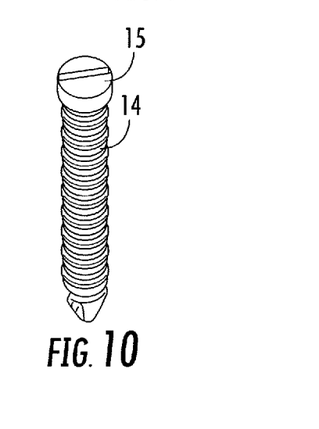
FIG. 10 is a pedicle screw.

The new pedicle screw assembly of the present invention will now be described with reference to FIGS. 2-19. A pedicle screw 14 is illustrated in FIG. 10. A reduction nut 34, FIG. 2, is employed to secure the remaining portion of the pedicle screw assembly to the pedicle screw. The reduction nut 34 permits the remaining portion of the pedicle screw assembly to pivot with respect to the pedicle screw 14, but does not allow it to be separated from the pedicle screw. A saddle assembly 36 is pivotally secured to the pedicle screw 14 by the reduction nut 34. The saddle assembly provides a seat for the placement and retention of a stabilization rod (not shown). Left and right retention members 38, FIG. 4, are located within the saddle assembly 36. The retention members 38 include legs 39. As illustrated, there are preferably four legs 39 on each retention member 38. The retention members 38 cooperate with CAM 40, FIGS. 5 and 6, to receive and retain a stabilization rod in a channel or trough 42. A stabilization rod would be held in position in channel 42, as illustrated in FIG. 8 by the reduction donut 44 and retention members 38.

Figure 5:
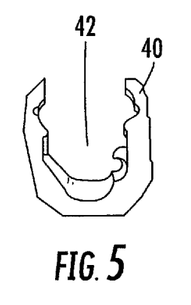
FIG. 5 is a CAM of the present invention in an "open" position.
Figure 6:
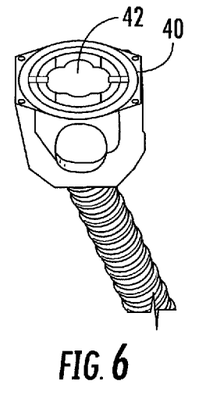
FIG. 6 is the CAM of FIG. 5 in a "closed" position.

In its "open" position, FIG. 5, CAM 40 is constructed and arranged to receive a stabilization rod. The retention members 38 are positioned within the CAM 40 such that the two longer legs 39 are adjacent the inner surface of 40 while the shorter legs 39 extend partially into the channel or trough 42. After the rod has been inserted in place, the CAM is closed to the position indicated in FIG. 6. In this position, the stabilization rod is securely held in place with respect to the pedicle screw 14 by the retention members 38 and the CAM. The CAM 40 can be rotated into its "closed" position with the use of a flat head or star shaped driver similar to the mechanism 28 on the end of tool 12. The CAM may or may not have a rigid inner surface (not shown) which stops the rod from slipping through the CAM and tulip.

In minimally invasive (percutaneous) procedures, cannulated tubes are utilized. These tubes can extend upwardly and out of the body cavity. This permits the surgeon or robot to move each of the pedicle screws and attached tulips, control angulation, to reposition the vertebrae of an individual to correct the spinal deformity problems; to help manipulate angulation and rotation, which may include Scoliosis. Alternatively, very long, medium length and normal length tulips can be employed. After the vertebrae are repositioned, stabilization rods are placed in the tulips and moved downwardly toward the lower portion of the tulip by a reduction donut 44 or similar device. After the stabilization rods are in their final position, and the CAM 40 has been placed in the locked position, the portion of the tulip above the reduction donut is broken off or removed.

Figure 7:
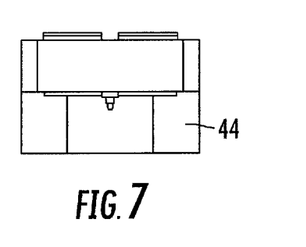
FIG. 7 is a reduction donut of the present invention.
Figure 8:
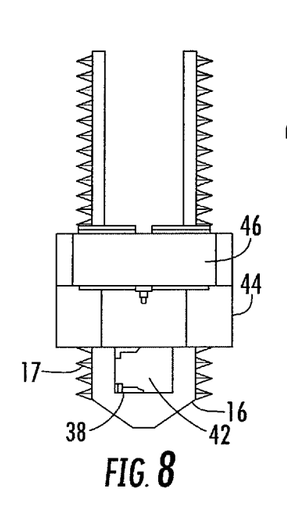
FIG. 8 is the reduction donut positioned on a tulip of a pedicle screw.
Figure 9A:
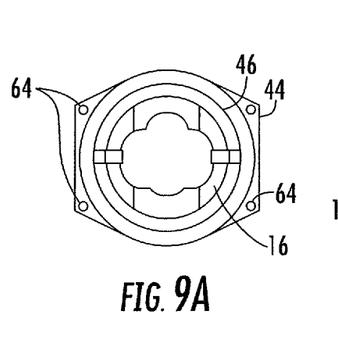
FIG. 9A is a top view of the assembly illustrated in FIG. 8.
Figure 9B:
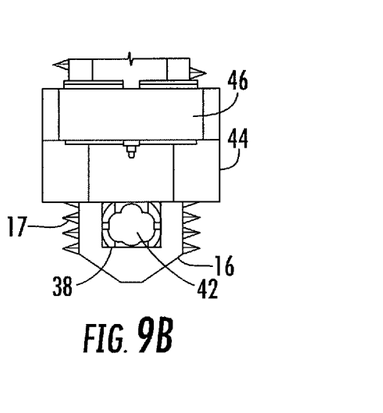
FIG. 9B is the reduction donut positioned on a tulip of a pedicle screw after the excess portion of the tulip has been removed.
Figure 11:
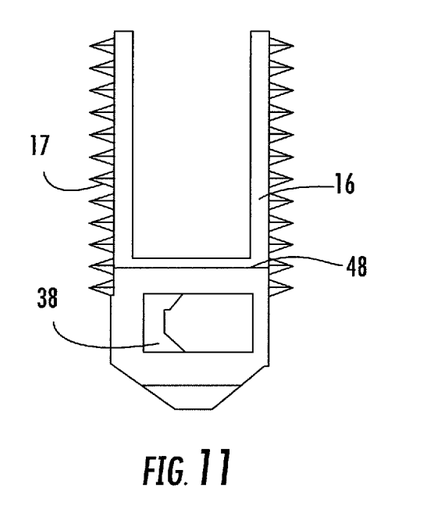
FIG. 11 is a tulip of the present invention.

A reduction donut 44 is illustrated in FIGS. 7-9. As illustrated in FIGS. 8 and 9, the reduction donut 44 is threadably secured to the outer surface of tulip 16. The reduction donut helps to secure the stabilization rod within the tulip 16. It also provides additional containment within the tulip and prevents the tulip from splaying apart since it compresses the tulip, rather than radially expanding the tulip like the prior art set screws. The reduction donut 44 can be made from a bio-absorbable material. In addition, portion 46 of reduction donut 44 can provide a bio-hermetic seal which is activated by heat from the body of the individual who is receiving the pedicle screw system. This enhances the sealing of the borders of the facet by breaking down and fusing. In addition, the entire reduction donut 44, including portion 46, can be made from steel, titanium, Nitinol, a bio-absorbable material, such as bio-glass, or a blend of these materials. The reduction donut 44 can also be round, 4, 6, or 8 sided, or in star shape or form, and have rounded or straight edge corners or other variations thereof. FIG. 8 is a side view and FIG. 9A is a top view of the complete tulip and reduction donut assembly in its final assembled condition. The reduction donut 44 is secured to the outer surface of the tulip 16 with threads 17 and holds a stabilization rod in trough 42. The elongated portion of the tulip 16 may be broken off above or below the reduction donut 44 after all the elements are in their final positions and secured together with the interlocking CAM 40. Scored lines, similar to line 48 in FIG. 11, may be provided at various locations along tulip 16 to assist the surgeon in breaking off portions of tulip 14. FIG. 11 illustrates a tulip 16 of the present invention. While the score line 48 is illustrated at a lower portion of tulip 16, it can be located at any portion along the tulip. Also, a plurality of score lines 48 can be formed on each tulip.

The reduction donut 44 or reduction sleeve 60 (FIGS. 14A and B) is then screwed onto the tulip and downwardly toward the stabilization rod. When all the rods are in their final positions, the reduction donuts, if utilized for the final construct, are completely tightened thereby securing the stabilization rods in their final positions. Then the retention member 38 is positioned in the lower portion of the tulip and in position to retain a stabilization rod. The retention member 38, see FIG. 4, is initially positioned with the legs 39 extending in horizontal direction. There are 4 legs 39 on each retention member 38 of the preferred embodiment. There can also be any number of legs 39 on each extension member. The extension member does not extend horizontally completely across the inner cross section of the tulip in the open position. The stabilization rod 50 is then inserted downwardly into the tulip 16 to one side of the retention member. The stabilization rod is in alignment with the U-shaped space 41 between the legs 39. The stabilization rod will rest in the lower U-shaped portion of the retention member. Next the retention member 38 is rotated approximately 90 degrees in a substantially horizontal plane. This locks the stabilization rod 50 between the legs 39 of the retention member 38 and within the tulip 16.

Figure 14A:
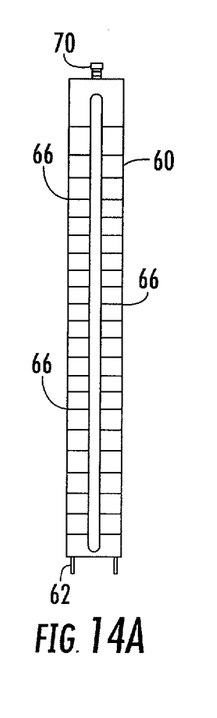
FIG. 14A is a side view of a reduction sleeve used to tighten the reduction donut.
Figure 14B:
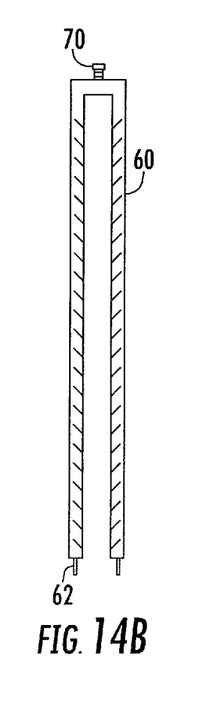
FIG. 14B is a front view of the reduction sleeve in FIG. 14A.
Figure 15A:
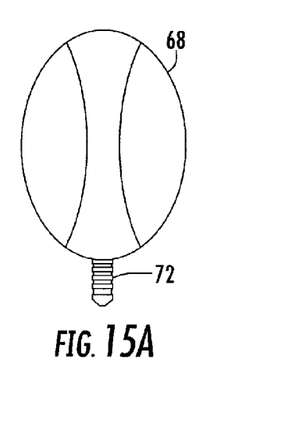
FIG. 15A is a handle, in a closed position, used to operate the reduction sleeve.
Figure 15B:
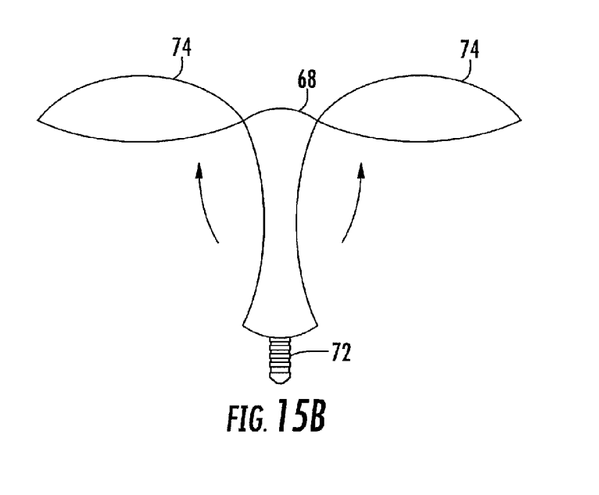
FIG. 15B is the handle in FIG. 15A in an open position.

Reduction sleeves 60, FIGS. 14 A and B, can optionally be utilized to thread and tighten the reduction donut 44 on tulip 16 or without the reduction donut 44 to reduce the rod 50 into final positioning. The reduction sleeves include a socket type of mechanism for interlocking the reduction donut, to tips 62 at one end thereof. This socket, prong or tip engages the outer edge of the reduction donut, or apertures or holes 64 in the reduction donut, FIG. 9A. The reduction sleeves also include depth marks 66 along the length thereof. These marks help the surgeon determine the depth that the stabilization rod has been inserted into an individual and thus its position with respect to the spine. Handle 68, FIGS. 15A and B can be secured to the top of the reduction sleeve 60 by cooperative couplings 70 and 72. The handle can also be provided with extensions or wings 74. These wings can be folded when not in use, as illustrated in FIG. 15A or extended when in use, as illustrated in FIG. 15B.

Figure 12:
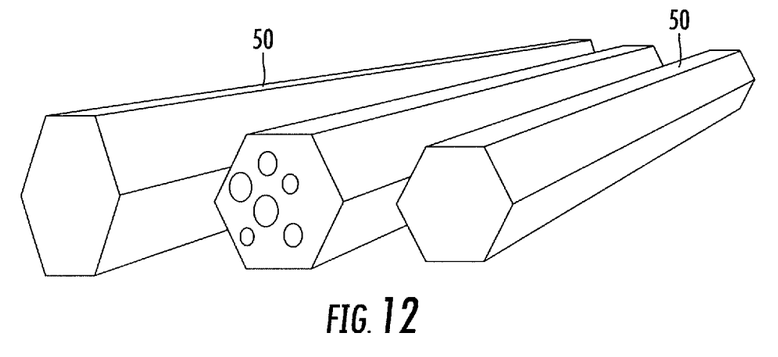
FIG. 12 are stabilization rods which can be employed in the present invention.

FIG. 12 illustrates a plurality of stabilization rods 50 which are octagonal in cross section. This type of rod is preferably employed in the present invention because of their ability to maintain their position and not rotate. The prior art stabilization rods are circular in cross section and thus will have a tendency to rotate about their longitudinal axis. The rods 50 of the present invention are not circular and therefore will not have a tendency to rotate about their longitudinal axis. While stabilization rods 50 are illustrated as being octagonal in cross section, they can be any shape in cross section. These rods can also come in various diameters that can be used in posterior cervical, thoracic, lumbar spine or elsewhere.

Figure 13:
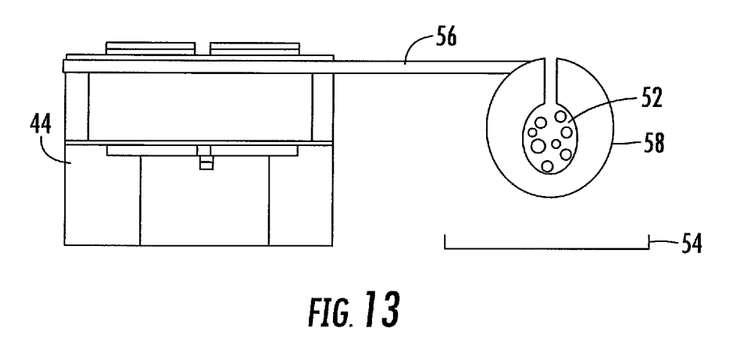
FIG. 13 is a view of a device used for placing a bioabsorbable material in a gutter along a plurality of vertebrae.

An optional feature of the present invention, illustrated in FIG. 13, is a device for securing a bio-absorbable material 52 into a gutter 54 which is constructed along a plurality of the vertebrae which are to be fused to each other. A rod or thin shaft 56 is secured to a reduction nut 44 or implantable rod or tulip and extends radially outwardly therefrom. A bio-absorbable material delivery pod 58 which contains bio-absorbable material 52 is secured to the end of rod 56. During the procedure, after all the stabilization rods 50 are secured and locked in position, the rods 56 can be moved and position the bio-absorbable material 52 within a gutter 54 formed along adjacent vertebrae. This bio-absorbable material helps fuse the vertebrae to each other.

Another optional feature of the present invention is the use of a Blocker that connects or snaps onto the rod to prevent the tulip 16 from slipping down the rod during methods of vertebral distraction. This small removable Blocker acts as a stopper.

Figure 16:
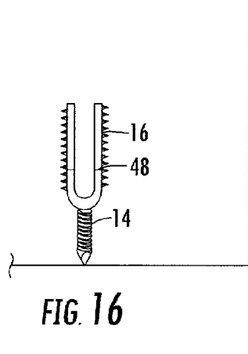
FIG. 16 is a pedicle screw and tulip of the present invention.

FIG. 16 illustrates a pedicle screw 14 and tulip 16 similar to the one illustrated in FIGS. 1 and 11. This type of tulip is open at the upper end thereof which permits stabilization rods 50 to be inserted therethrough the upper open end. These tulips are typically 40 mm long, but can be made in any length. A score line or breakaway portion 48 on the tulip enables the surgeon to remove the portion of the tulip which is not required after the stabilization rods have been secured to the tulips and moved into their final positions. While one score line 48 is illustrated, there can be a plurality of score lines 48 on each tulip.

Figure 17:
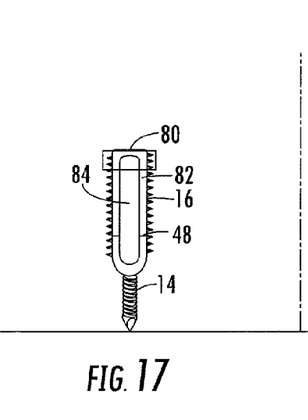
FIG. 17 is a tulip/tube extension of the present invention.
Figure 18:
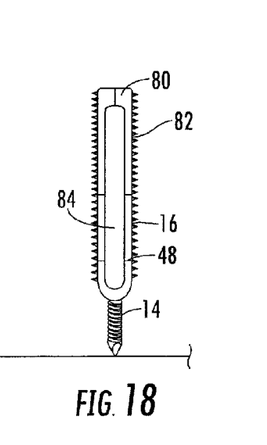
FIG. 18 is a tulip/tube extension similar to the one illustrated in FIG. 17.

FIG. 17 illustrates a "closed tulip/tube" 16. The tulip/tube 16 has a closed upper end 80, as can be seen in FIGS. 17 and 18. A tube 82 is secured to the outer portion of tulip 16 and extends substantially the length of tulip 16. The tube 82 and tulip 16 are preferably 80 mm long, but can be made in any length. The extra length provided by the tube 82 enables the surgeon to better manipulate the tulip and stabilization rod for proper positioning within the patient. The closed tulip/tube in FIG. 17 has a reduction donut 44 at an upper end thereof. The stabilization rod 50 is placed into the slotted opening 84 in the tulip and the donut is tightened to move the rod 50 into its final position as determined by the surgeon. Subsequently, the portion of the tulip/tube 16 that is not required can be broken off at a score line 48 and removed from the patient.

FIG. 18 illustrates a "closed tulip/tube" 16 similar to the one illustrated in FIG. 17. The tulip/tube 16 has a closed upper end 80, as can be seen in FIGS. 17 and 18. A tube 82 is secured to the outer portion of tulip 16 and extends substantially the length of tulip 16. The tube 82 and tulip 16 are preferably 120 mm long, but can be made in any length. The extra length provided by the tube 82 enables the surgeon or robot to better manipulate the tulip and stabilization rod for proper positioning within the patient. The closed tulip/tube in FIG. 17 has a reduction donut 44 at an upper end thereof. The stabilization rod 50 is placed into the slotted opening 84 in the tulip and the nut is tightened to move the rod 50 into its final position as determined by the surgeon. The nut can also be descended down upon the rod and not tightened for utilization in a "Growing Rod" application where the rod has the ability to slightly shift as the patient grows in height. The locking CAM incorporated in the closed position can have a smooth inner surface to allow for this as well. Subsequently, the portion of the tulip/tube 16 that is not required can be broken off at a score line 48 and removed from the patient.

Figure 19:
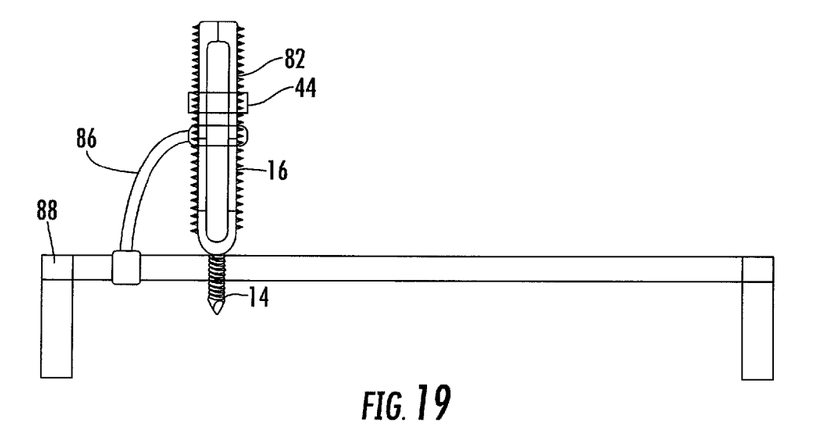
FIG. 19 is an embodiment of the present invention wherein an arm is employed to secure the tulip/tube.
Figure 20:
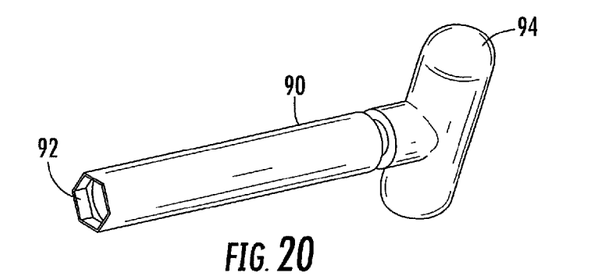
FIG. 20 is a torque/final lock driver.
Figure 21:
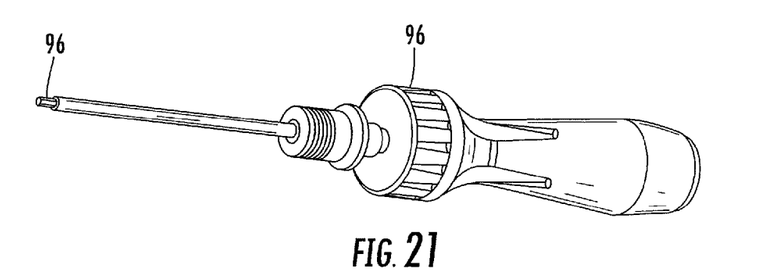
FIG. 21 is a pedicle screwdriver.
Figure 22:
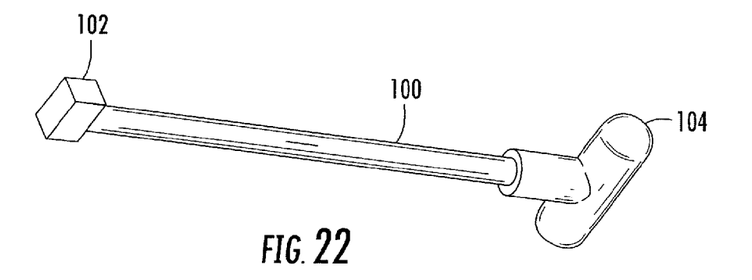
FIG. 22 is a CAM lock driver.

FIG. 19 illustrates another feature of the present invention. When an extended tulip/tube, such as the ones illustrated in FIGS. 17 and 18 is employed, an arm 86 can secure the tulip/tube to the surgical table 88 or other stationary object. This arrangement enables a surgeon or robot to work with complex three dimensional deformities which require specific vertebral rotation to correct. The arms 86 also enable the surgeon or robot to work with less assistance. The tube extension 82 enable the surgeon to derotate, push or pull on the pedicle screw and tulip to correctly position them and/or readily enable insertion of the stabilization rod 50. After final adjustments are made the reduction donut 44 is tightened and the system of the present invention is secured in its final position. The arms 86 enable multiple pedicle screws and tulips to be manipulated to receive and adjust one or more stabilization rods 50. This gives the surgeon or robot more control, a safer reduction with optimal vertebral derotation. FIG. 20 illustrates a reduction nut driver 90. One end of the reduction nut driver 90 includes a fitting 92 which is constructed and arranged to fit onto and rotate reduction donut 44. The center portion of the nut driver is hollow, which permits the elongate portion of tulip 16 to pass therein and thereby enable donut 44 to be tightened onto a rod. The end of the nut driver 90 opposite the fitting 92 includes a handle 94 which facilitates the rotation of the nut driver 90. FIG. 21 illustrates a screwdriver 96. The screwdriver includes a tip 98 which is shaped to engage the recess in the head 15 of a bone screw 14. FIG. 22 illustrates a CAM lock driver 100. This tool includes an end 102 which engages the CAM 40 to rotate the CAM from its open position to its closed position, as described herein. The end of the CAM lock driver opposite end 102 includes a handle 104 which facilitates the rotation of the CAM lock driver 100.

Figure 23:
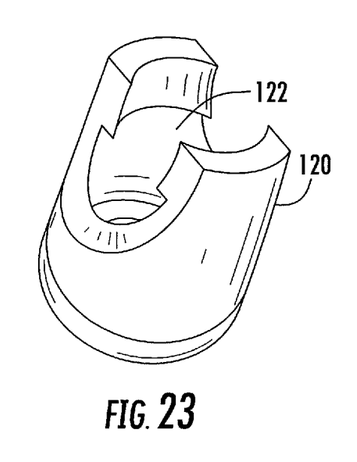
FIG. 23 is a lower portion of a tulip.
Figure 24:
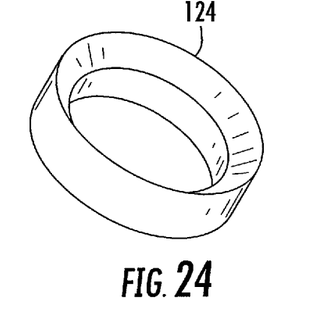
FIG. 24 is a cradle in which a tulip fits.
Figure 25:
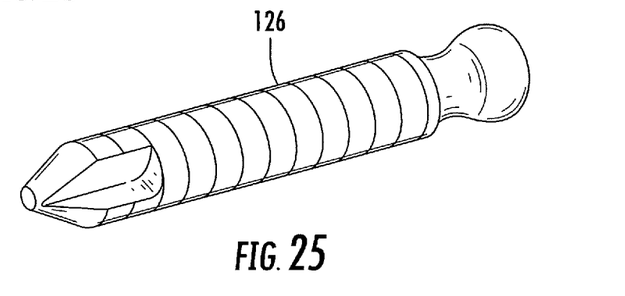
FIG. 25 is a pedicle screw.

FIG. 23 illustrates a lower portion of a tulip 120 similar to tulip 16, illustrated in FIG. 11. This lower portion 122 of the tulip is adapted to receive and hold the CAM 40 and retention members 38. The cradle 124 illustrated in FIG. 24 is similar in shape and function to the reduction nut 34, illustrated in FIG. 2. The cradle permits polyaxial movement of the tulip on the pedicle screw. FIG. 25 is another example of a type of pedicle screw 126 which can be employed in the present invention.

Figure 26:
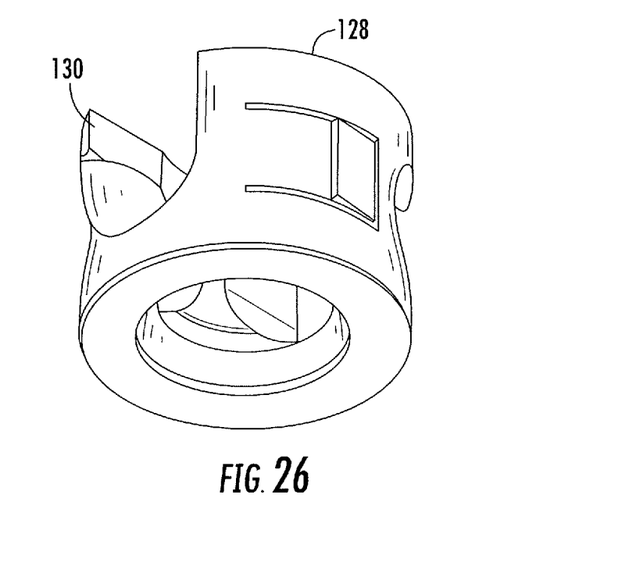
FIG. 26 is a CAM lock.
Figures 30, 31:
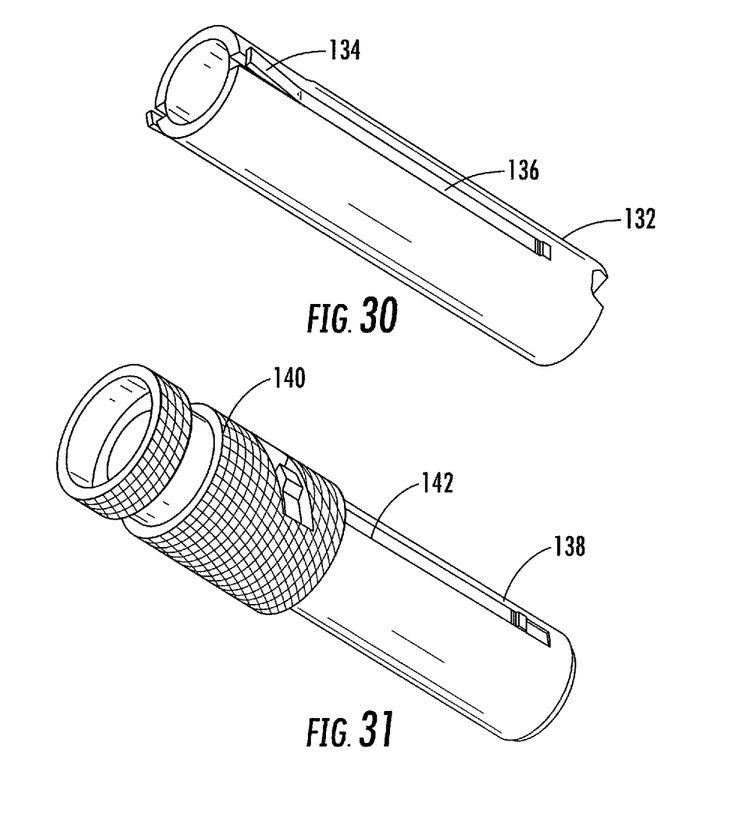
FIG. 30 is a first embodiment of a tool to unlock the CAM lock.
FIG. 31 is a second embodiment of a tool used to unlock the CAM lock.
Figure 32:
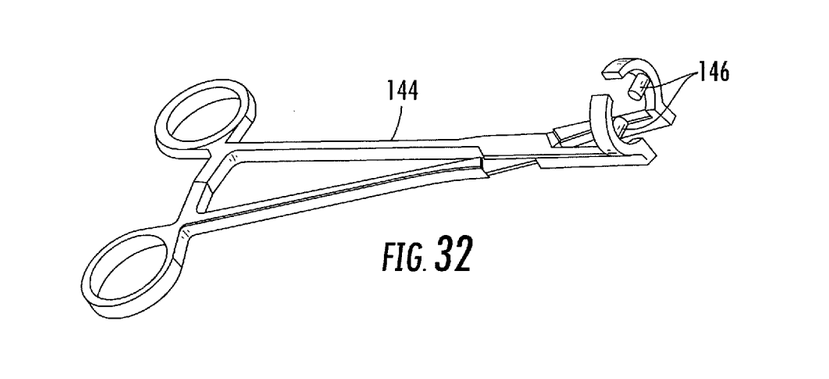
FIG. 32 is a third embodiment of a tool used to unlock the CAM lock.

FIG. 26 illustrates another type of CAM lock 128 that can be employed in the present invention. Pivoting elements 130 on the CAM lock 128 permit the insertion of rods, similar to the stabilization rods 50 illustrated in FIG. 12. The pivoting elements 130 are first pivoted to their open position, illustrated in FIG. 26. Next they are pivoted toward the CAM into their closed position. In their closed position, the engage and retain the rods within the tulips. FIGS. 30-32 illustrated three different tools which can be employed to loosen and open the CAM lock so that rods 50 can be removed or readjusted. A first embodiment 132 of the CAM lock loosening tool is illustrated in FIG. 30. A plurality of levers 134 are positioned on opposite sides of the tool. When these levers are moved toward the tool 132, they move elongate elements 136 downward, which in turn engages portions of the CAM and opens it. A second embodiment 138 of the CAM loosening tool is illustrated in FIG. 31. A collar 140 is positioned on an upper portion of the tool 138. When the collar 140 is turned in a counter-clockwise direction it moves elongate elements 142 downward which in turn engages portions of the CAM and opens it. A third embodiment 144 of the CAM loosening tool is illustrated in FIG. 32. This embodiment functions similar to a retractor. When the retractor is closed, pins 146 engage the CAM and open it.

Figure 27:
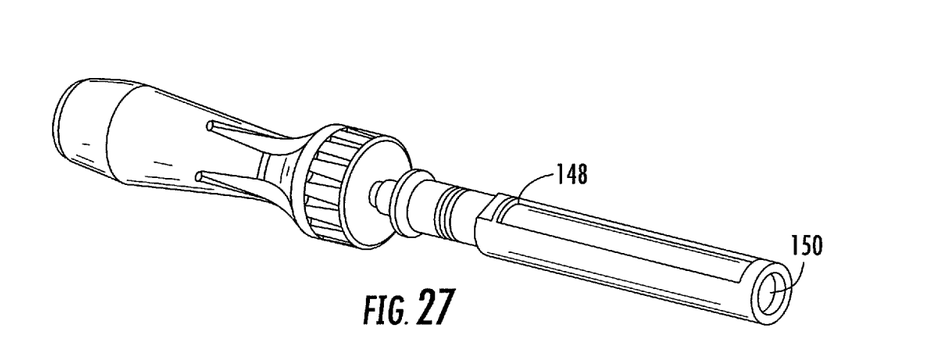
FIG. 27 is a reducing wrench.
Figure 28:
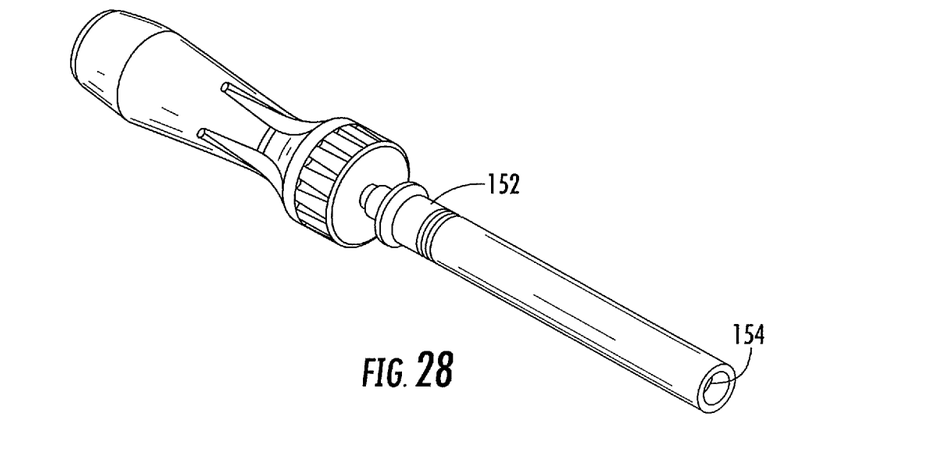
FIG. 28 is a pedicle screwdriver.
Figure 29:
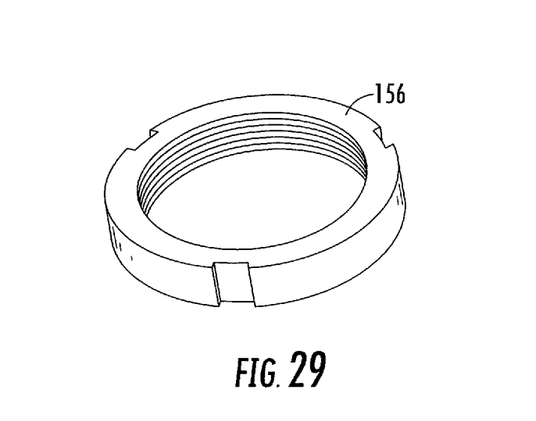
FIG. 29 is a lock nut used on a tulip.

FIG. 27 is an example of a reducing tool 148 which is used to manipulate the tulip 16. The hollow central portion 150 of tool 148 is sized to fit over and engage the tulip 16 so that it can be manipulated into the correct position. The tool can also be employed to break off excess portions of the tulips. FIG. 28 illustrates an example of a screwdriver 152 which can be used to insert the pedicle screw. The screwdriver 152 includes a tip 154 which is designed to fit into and engage the hollow portion on the top of a pedicle screw. FIG. 29 illustrates a lock nut 156 which can be used to secure reduction donut 44 in place.

Another optional feature of the present invention is the use of Nitinol on the tip of the pedicle screw(s). This permits the tip or other portion of the pedicle screw(s) to be formed in such a manner and/or with features to promote anchoring the screw into the bone. The tip of the pedicle screw can be formed with projections or in a shape which will enhance its retention in a bone. Prior to installation of the pedicle screw, the screw is cooled so that the projections will retract toward the screw or the shape of the screw will be reduced so as to permit easily installation of the pedicle screw. Once the screw is warmed by contact with the bone, the projections will expand and/or the shape of the screw will change so that it will present a larger surface to engage the bone, and thus the screw will become very difficult to remove from the bone. For example, the cross section of the tip of the pedicle screw can be in a star shape which contracts when cooled and expands when heated, such as by being in proximity to a bone in an individual. An FDA approved coolant can be employed to later retract the screw in the event of a revision if necessary.

Another optional feature of the present invention is the use of Radio Frequency Identification (RFID) or Haptic sensors. An RFID or Haptic sensor can be placed at the top of or embedded in the pedicle screw and/or instruments, and a radio or haptic receiver can be placed in the tool 12, or as a separate reader and/or computer system nearby the patient, whereby a surgeon, robot, or remote user has a positive indication or through tactile feel that the tool 12 has engaged and manipulated the pedicle screw 14, another tool or implantable device, the rod 50, the tulip 16, or the tip of the HOLDING Wire, Jam Shidi, Pedicle Probe, Tap, or Screwdriver. The RFID or Haptic sensor can also be placed on the tulip 16, pedicle screw 14, another tool or implantable device, rod 50, or tool 12. The use of the RFID or Haptic sensors can assist in remote or precise robotic placement of the tools, pedicle screw, and rod. The sensors can be used to measure the exact positioning of the tools or implants in the procedure. The sensors can also interface with pre-operative or inter-operative CT scanners for three dimensional measurements, manipulation, either remotely, automatically, or robotically. The sensors can also be used with a surgeon user interface to establish tactile feel of the instruments and implants used during the procedure. The sensors can also be used to measure the depth of the instruments and implements, and used for comparison with adjacent levels. The sensors may also be used to measure rod length or growth. The sensors may also be used to manipulate the patients' implants from outside of the body. The sensors may also be used to measure degree of rotation or derotation, the tulip alignment, or degree of reduction during or after the procedure.

Figure 33:
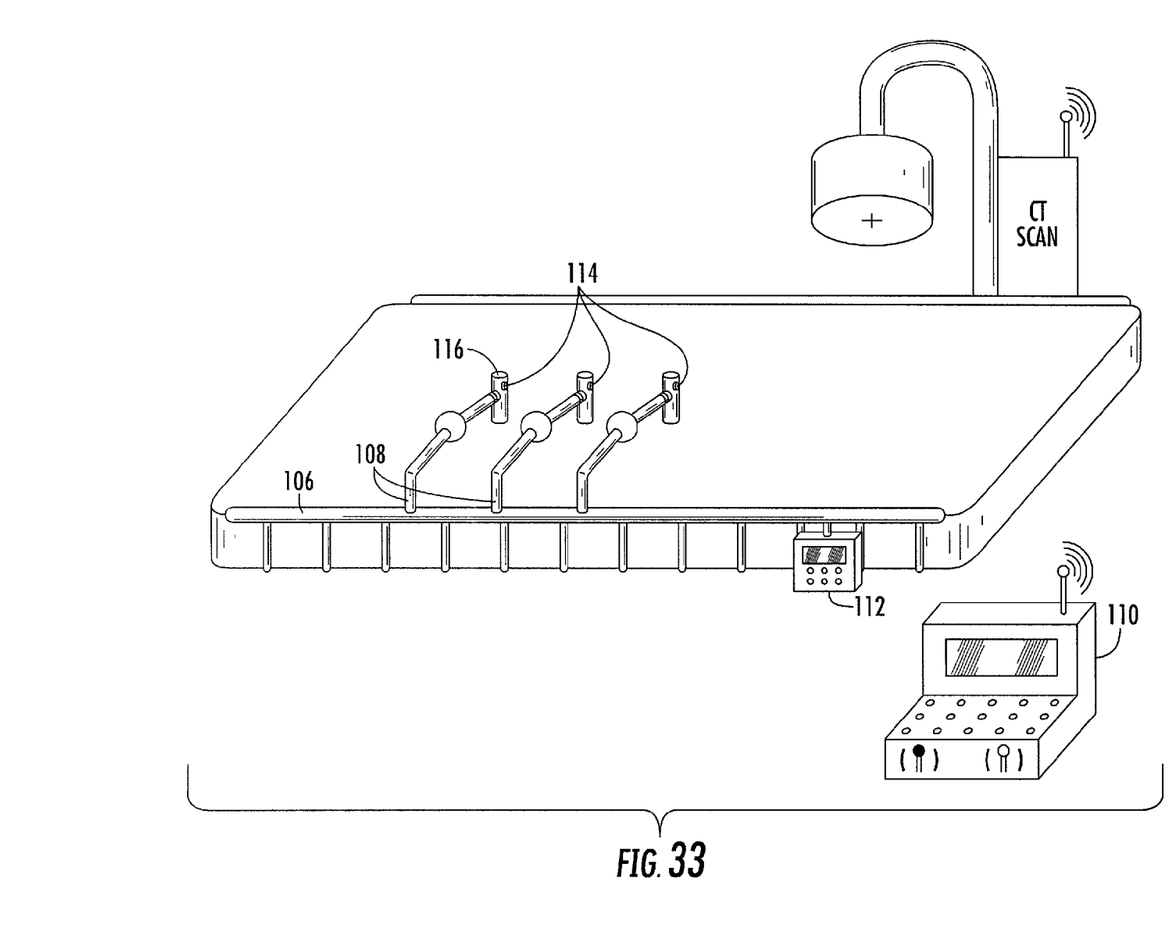
FIG. 33 is a robotic system for the installation of pedicle screws and rods in an individual.

FIG. 33 illustrates another optional feature of the present invention wherein the use of a bedrail 106, bedrail adapter, articulating arm, or telescopic bedrail, that has an extension arm 108 and/or tool that reaches out to a device that can hold a rod holder, wrench-like in form, or tool that can attach to the elongated tulip 16 and/or rod 50 to control or manipulate vertebral derotation by the surgeon or robot. The tool may be manually or robotically controlled. The surgeon or robot may use a method incorporating hydraulics or mechanics that are controlled and measured through a remote interface by the operator, or done by the machine automatically. An advantage of this feature is that it enables the surgeon, or Haptic controlled computer machine interface, or RFID and Haptic controlled robot to place rods simultaneously to reduce spinal deformity which will give the surgeon, or RFID and/or Haptic computer integrated system, more control, precision placement, a safer reduction, fasted procedural process and optimal vertebral derotation. The sensors may also provide a tactile feeling which will give the operator a better sense of dimensional placement and manipulation. A remote control device 110 is operated by a surgeon. Signals from the remote control device 110 are received by a control module 112. The control module operates the robotic arms 108 which install the pedicle screw and rod system. The robotic arms 108 include holders 114 which hold, manipulate and install the pedicle screws. The holders 114 include sensors 116 which pick up signals from RFID devices or Haptic sensors installed on the pedicle screws. The robotic arms 108 can be operated mechanically or hydraulically. The sensors 116 provide information to the remote control device 110 which, in conjunction with robotic software, enables a surgeon to accurately install pedicle screws into individual patients. Different sensors 116 are employed, depending upon the means, to activate the holders 114. For example, if hydraulics are employed to activate the holders, the sensors need to know that any slight increase or decrease in pressure is directly transmitted to the holders 114. If a mechanical connection is employed instead, there is some pressure which can be absorbed by the mechanism transmitting the signals to the holders. The sensors 116 need to be designed and programmed so that too much pressure will not be exerted on the holders 114, and in turn on the pedicle screws and tulips.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A bone screw comprising:
   an elongate screw portion, said screw portion having a head and a threaded portion;
   a cylindrical element pivotably secured to said head, said cylindrical element including a receiving portion for receiving a rod, said cylindrical element having a substantially U-shaped cross section including two upwardly extending legs, said legs having threads on an exterior portion thereof, said cylindrical element including a saddle assembly positioned at a lower portion of said cylindrical element, said saddle assembly including a plurality of retention members, said retention members being substantially U-shape, each of said U-shaped retention members having one leg of said U-shape shorter than another leg of said U-shape, said retention members are constructed and arranged to retain a rod when inserted in said saddle assembly; and
   a reduction sleeve threadably secured to said upwardly extending legs, said reduction sleeve retaining a rod secured in said saddle assembly when said reduction sleeve is screwed toward said screw portion.

2. The bone screw of claim 1 wherein said head includes a recessed portion, said recessed portion being constructed and arranged to be engaged by a tool to rotate said bone screw whereby said bone screw is installed in a bone.

3. The bone screw of claim 2 wherein each leg of said retention members is substantially U-shaped, said retention members are positioned within said saddle assembly with the open ends of said u-shaped retention members facing away from said bone screw and are in a position to accept a rod which can be inserted therein.

4. The bone screw of claim 3 wherein each of said retention members are rotated within said saddle assembly with the open ends of each of said U-shaped retention member facing each other whereby a rod can be retained therein.

5. The bone screw of claim 1 wherein each leg of said retention members is substantially U-shaped, said retention members are positioned within said saddle assembly with the open ends of said U-shaped retention members facing away from said bone screw and are in a position to accept a rod which can be inserted therein.

6. The bone screw of claim 5 wherein each of said retention members are rotated within said saddle assembly with the open ends of each of said U-shaped retention members facing each other whereby a rod can be retained therein.

7. The bone screw of claim 1 wherein said cylindrical element includes a portion which is broken off subsequent to a rod being inserted within said cylindrical element and said reduction sleeve being screwed into its final position.

8. A system for installing a bone screw and a rod to a bone comprising:
   a bone screw, said bone screw including an elongate screw portion, said screw portion having a head and a threaded portion;
   a cylindrical element pivotably secured to said head, said cylindrical element including a receiving portion for receiving a rod, said cylindrical element having a substantially U-shaped cross section including two upwardly extending legs, said legs having threads on an exterior portion thereof, said cylindrical element including a saddle assembly positioned at a lower portion of said cylindrical element, said saddle assembly including a plurality of retention members, said retention members being substantially U-shape, each of said U-shaped retention members having one leg of said U-shape shorter than another leg of said U-shape, said retention members are constructed and arranged to retain a rod when inserted in said saddle assembly;

a reduction sleeve threadably secured to said upwardly extending legs, said reduction sleeve retaining a rod secured in said saddle assembly when said reduction sleeve is screwed toward said screw portion; and a tool constructed and arranged to insert said bone screw into a bone.

9. The system for installing a bone screw and a rod of claim 8 wherein said head includes a recessed portion, said recessed portion being constructed and arranged to be engaged by a tool to rotate said bone screw, whereby said bone screw is installed in a bone, said tool includes a portion which engages said recessed portion of said head whereby said bone screw can be threadably inserted into a bone.

10. The system for installing a bone screw and a rod of claim 9 wherein each leg of said retention members is substantially U-shaped, said retention members are positioned within said saddle assembly with the open ends of said U-shaped retention members facing away from said bone screw and are in a position to accept a rod which can be inserted therein.

11. The system for installing a bone screw and a rod of claim 10 wherein each of said retention members are rotated within said saddle assembly with the open ends of each of said U-shaped retention members facing each other, whereby a rod can be retained therein.

12. The system for installing a bone screw and a rod of claim 8 wherein each leg of said retention members is substantially U-shaped, said retention members are positioned within said saddle assembly with the open ends of said U-shaped retention members facing away from said bone screw and are in a position to accept a rod which can be inserted therein.

13. The system for installing a bone screw and a rod of claim 12 wherein each of said retention members are rotated within said saddle assembly with the open ends of each of said U-shaped retention members facing each other, whereby a rod can be retained therein.

14. The system for installing a bone screw and a rod of claim 8 wherein said cylindrical element includes a portion which is broken off subsequent to a rod being inserted within said cylindrical element and said reduction sleeve being screwed into its final position.

15. The system for installing a bone screw and a rod of claim 9 wherein said tool includes a member that is constructed and arranged to engage said cylindrical element, said member having an outer portion which engages the threads on the exterior portion of said cylindrical element, said member also including an inner member which engages the interior of said cylindrical member, whereby said tool can be secured to said cylindrical member attached to said bone screw and said portion of said tool which engages said recessed portion of said head of said bone screw can be guided into engagement with said recessed portion of said head of said bone screw.

16. The system for installing a bone screw and a rod of claim 8 wherein said bone screw and said tool each include a hollow central portion, said hollow central portions permitting said bone screw and said tool to be inserted in a bone utilizing a HOLDING wire.

17. The system for installing a bone screw and a rod of claim 8 wherein a height of said reduction sleeve is relatively short compared to said cylindrical element, a reduction sleeve installation member is removably secured to said reduction sleeve, whereby rotation of said reduction sleeve installation member rotates said reduction sleeve and advances said reduction sleeve toward said bone screw and enables said reduction sleeve to secure a rod to said bone screw.

18. The system for installing a bone screw and a rod of claim 17 including a handle securable to said reduction sleeve installation member, said handle including a plurality of wings, said wings being movable between a stored position and an extended operative position, said operative position enables an operator to apply a large amount of torque to said reduction sleeve installation member and thus said reduction sleeve, whereby said reduction sleeve can be secured to said cylindrical element so as to prevent loosening of said reduction sleeve.

19. The system for installing a bone screw and a rod of claim 8 including a tube surrounding and secured to said cylindrical element, said tube being operable by an individual to position said cylindrical element for reception of said rod.

20. The system for installing a bone screw and a rod of claim 8 wherein the tip of said bone screw is made from Nitinol, said tip of said bone screw being constructed and arranged to change shape upon an application of heat to said tip.

21. The system for installing a bone screw and a rod of claim 8 including RFID devices in said bone screw.

22. The system for installing a bone screw and a rod of claim 21 including a plurality of holders constructed and arranged to hold, manipulate and install said bone screw and cylindrical element, said plurality of holders being operatively connected to a control module;

a remote control device in communication with said control module, said remote control device being operable to receive instructions from an operator and communicate said instructions to said control module, whereby said plurality of holders are manipulated by said instructions to install said bone screw.

23. The system for installing a bone screw and a rod of claim 22 wherein said plurality of holders are hydraulically operated.

24. The system for installing a bone screw and a rod of claim 22 wherein said plurality of holders are mechanically operated.

* * * * *